US008095212B2

(12) United States Patent
Sato

(10) Patent No.: US 8,095,212 B2
(45) Date of Patent: Jan. 10, 2012

(54) HIGH-FREQUENCY SURGICAL APPARATUS AND HIGH-FREQUENCY SURGICAL METHOD FOR CLOSURE OF PATENT FORAMEN OVALE

(75) Inventor: Taisuke Sato, Hachioji (JP)

(73) Assignees: Olympus Medical Systems Corp., Tokyo (JP); Terumo Kabushiki Kaisha, Tokyo (JP)

(*) Notice: Subject to any disclaimer, the term of this patent is extended or adjusted under 35 U.S.C. 154(b) by 519 days.

(21) Appl. No.: 12/257,909

(22) Filed: Oct. 24, 2008

(65) Prior Publication Data
US 2010/0106158 A1 Apr. 29, 2010

(51) Int. Cl.
*A61B 5/05* (2006.01)
(52) U.S. Cl. .................. 600/547; 606/51; 606/52
(58) Field of Classification Search .......... 600/547; 604/42, 50–52
See application file for complete search history.

(56) References Cited

U.S. PATENT DOCUMENTS

| | | | |
|---|---|---|---|
| 2003/0093071 A1* | 5/2003 | Hauck et al. ............... 606/41 |
| 2006/0100619 A1* | 5/2006 | McClurken et al. ......... 606/45 |
| 2006/0184048 A1 | 8/2006 | Saadat | |
| 2007/0112347 A1* | 5/2007 | Malecki et al. ............. 606/41 |
| 2008/0082100 A1* | 4/2008 | Orton et al. ................. 606/52 |
| 2008/0140113 A1* | 6/2008 | Taimisto et al. ........... 606/213 |
| 2009/0005780 A1 | 1/2009 | Kato | |
| 2009/0069810 A1* | 3/2009 | Kuroda et al. .............. 606/51 |
| 2010/0094276 A1* | 4/2010 | Kabaya et al. ............. 606/34 |

FOREIGN PATENT DOCUMENTS

| | | |
|---|---|---|
| JP | 05-337131 | 12/1993 |
| JP | 08-317935 | 12/1996 |
| JP | 2004-512859 | 4/2004 |
| JP | 2005-000225 | 1/2005 |
| JP | 2007-519489 | 7/2007 |
| JP | 2007-195980 | 8/2007 |
| JP | 2008-036439 | 2/2008 |
| JP | 2008-528239 | 7/2008 |
| JP | 2009-527258 | 7/2009 |
| WO | WO 01/80724 A2 | 11/2001 |
| WO | WO 2005/074517 A2 | 8/2005 |
| WO | 2006/083794 A2 | 8/2006 |
| WO | WO 2007/100067 A1 | 9/2007 |

OTHER PUBLICATIONS

International Search Report dated Dec. 15, 2009.

* cited by examiner

*Primary Examiner* — Nicholas Lucchesi
*Assistant Examiner* — Gerald Landry, II
(74) *Attorney, Agent, or Firm* — Scully, Scott, Murphy & Presser, P.C.

(57) ABSTRACT

A high-frequency surgical PFO closure apparatus used to treat patent foramen ovale in the heart includes first and second electrodes which grasp living tissue of the patent foramen ovale; a high-frequency power supply section which supplies high-frequency power to the living tissue via the electrodes; an impedance measuring section which measures an impedance value by supplying high-frequency power to the living tissue; a grasping condition determining section which determines, based on the measured impedance value, a grasping condition regarding how the living tissue is grasped in blood by the electrodes; and a control section which controls high-frequency power supply at a predetermined power level needed to treat the patent foramen ovale, according to a result of the determination.

15 Claims, 13 Drawing Sheets

FIG.13

| MEASURED IMPEDANCE [Ω] | ON/OFF TIMES [sec] | | |
|---|---|---|---|
| | SET OUTPUT: 0 - 20 W | SET OUTPUT: 21 - 40 W | SET OUTPUT: 41 - 60 W |
| 0 – 20 | 0.4/10 | 0.2/10 | 0.1/10 |
| 21 – 40 | 0.6/10 | 0.3/10 | 0.2/10 |
| 41 – 60 | 1.0/10 | 0.5/10 | 0.3/10 |
| 61 – 200 | 1.4/10 | 0.7/10 | 0.3/10 |
| 200 OR ABOVE | STOP OUTPUT | | |

# HIGH-FREQUENCY SURGICAL APPARATUS AND HIGH-FREQUENCY SURGICAL METHOD FOR CLOSURE OF PATENT FORAMEN OVALE

BACKGROUND OF THE INVENTION

1. Field of the Invention

The present invention relates to a high-frequency surgical apparatus and high-frequency surgical method for closure of patent foramen ovale, the apparatus and method being used to treat patent foramen ovale (PFO) in the heart.

2. Description of the Related Art

There is a condition known as patent foramen ovale (PFO). The PFO is a flaplike opening in part of the atrial septum which separates the left atrium from the right atrium in the heart. Normally, the pressure in the left atrium is higher than the pressure in the right atrium, closing the patent foramen ovale by pressing it into contact with the atrial septum. However, severe coughing or tension (due to pressure on the lungs) can reverse the pressure difference, temporarily opening the flap.

Blood may contain blood clots developed in the body. Normally, the blood returning to the right atrium from the body is sent to the lungs where any blood clot is removed. However, it may happen that the instant the PFO opens, a blood clot passes through the PFO and sent back to the body. If the blood clot reaches the brain, it can cause cerebral infarction. To prevent cerebral infarction, it is desirable to close the PFO.

For example, PCT International Publication No. WO 2007/100067 discloses a high-frequency surgical apparatus which closes a PFO using high-frequency power. The conventional example involves grasping a PFO by grasping means which includes a needle member and grasping member, applying high-frequency power to the needle member and grasping member serving as high-frequency electrodes, and heating and closing the PFO by Joule heating.

SUMMARY OF THE INVENTION

The present invention provides a high-frequency surgical apparatus for closure of patent foramen ovale, the high-frequency surgical apparatus being used to treat patent foramen ovale in the heart, includes:
- a first and second electrodes which grasp living tissue of the patent foramen ovale, at least one of the first and second electrodes being capable of puncturing the living tissue;
- a high-frequency power supply section which supplies high-frequency power to the living tissue via the first and second electrodes;
- an impedance measuring section which measures an impedance value with the living tissue acting as a load when high-frequency power is supplied to the living tissue from the high-frequency power supply section;
- a grasping condition determining section which determines, based on the impedance value measured by the impedance measuring section, a grasping condition regarding how the living tissue is grasped in blood by the first and second electrodes; and
- a control section which controls high-frequency power supply to the living tissue at a predetermined power level needed to treat the patent foramen ovale, according to a determination result produced by the grasping condition determining section.

The present invention provides a high-frequency surgical method for closure of patent foramen ovale, the high-frequency surgical method being used to treat patent foramen ovale in the heart, includes:
- a grasping step of grasping living tissue of the patent foramen ovale using a first and second electrodes, at least one of the first and second electrodes being capable of puncturing the living tissue;
- a high-frequency power supply step of supplying high-frequency power at a low power level to the living tissue via the first and second electrodes;
- an impedance measuring step of measuring an impedance value with the living tissue acting as a load when high-frequency power at the low power level is supplied to the living tissue from the high-frequency power supply step;
- a grasping condition determining step of determining, based on the impedance value measured by the impedance measuring step, a grasping condition regarding how the living tissue is grasped in blood by the first and second electrodes; and
- a control step of controlling high-frequency power supply at a predetermined power level needed to treat the patent foramen ovale, according to a determination result produced by the grasping condition determining step.

BRIEF DESCRIPTION OF THE DRAWINGS

FIGS. 1 to 10 relate to a first embodiment of the present invention, where:

FIG. 1 is a perspective view showing appearance of a high-frequency surgical PFO closure apparatus according to the first embodiment of the present invention;

FIG. 2 is an external view of a distal side of a high-frequency probe;

FIG. 3 is a block diagram showing a configuration of the high-frequency surgical PFO closure apparatus according to the first embodiment;

FIG. 4 is an explanatory diagram showing a PFO and its vicinity in the heart;

FIG. 5 is an explanatory diagram showing a grasping electrode section at a distal end of the high-frequency probe with the grasping electrode section set to close PFO;

FIG. 6 is a flowchart showing processing procedures of a high-frequency surgical method according to the first embodiment;

FIG. 8 is a block diagram showing a partial configuration of a high-frequency surgical apparatus according to a variation of the first embodiment;

FIG. 9 is a flowchart showing processing procedures of a high-frequency surgical method according to the variation;

FIG. 10 is an operation chart illustrating time variation of an impedance value displayed on a display section according to the variation;

FIG. 13 is a chart showing content of a control table; and

DETAILED DESCRIPTION OF PREFERRED EMBODIMENTS

Embodiments of the present invention will be described below with reference to the drawings.

First Embodiment

Figure 1:
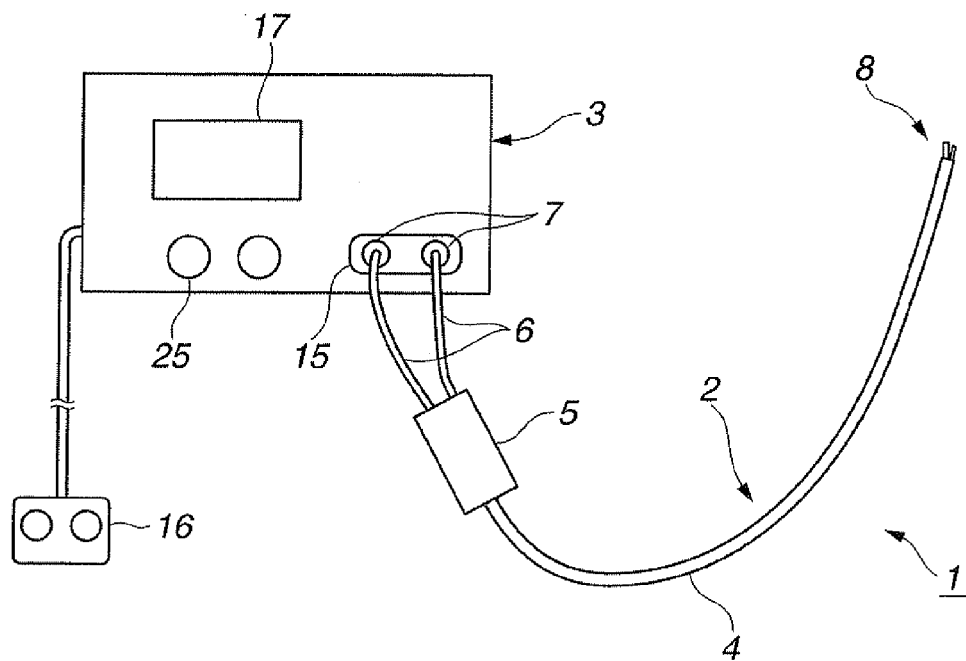

As shown in FIG. 1, a high-frequency surgical apparatus for closure of patent foramen ovale (hereinafter referred to as a high-frequency surgical PFO closure apparatus) 1 according to a first embodiment of the present invention includes a high-frequency probe 2 serving as a surgical instrument or treatment instrument for closing patent foramen ovale (PFO) (described later) in the heart and a high-frequency surgical power supply system 3 which supplies high-frequency power to the high-frequency probe 2.

The high-frequency probe 2 includes an elongated, flexible catheter 4 which can be inserted into a blood vessel, a grasping section 5 installed at a rear end of the catheter 4 in order to be grasped by a surgeon, and a high-frequency cable 6 extending from the grasping section 5. A connector 7 at an end of the high-frequency cable 6 is detachably connected to the high-frequency surgical power supply system 3.

Figure 2:
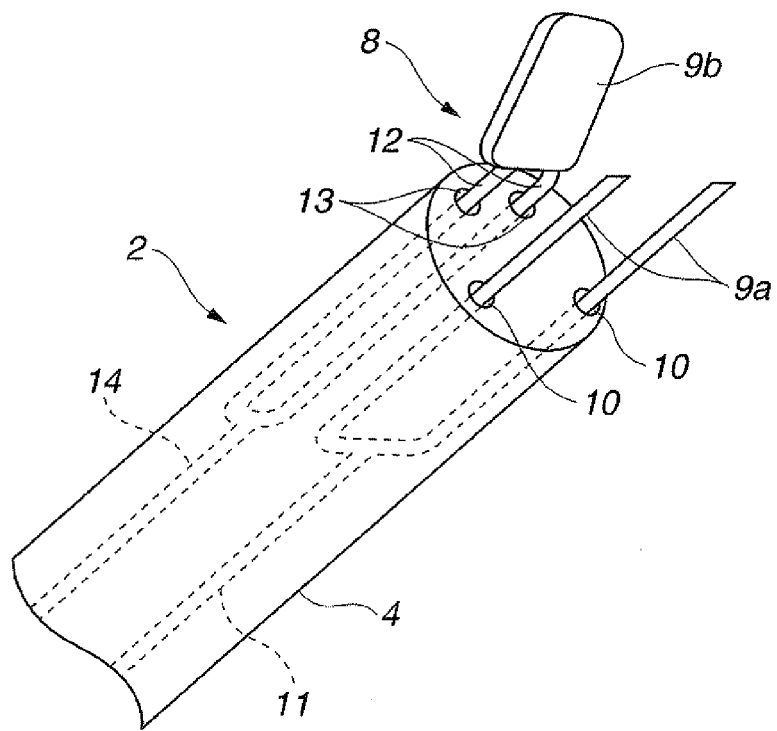

A grasping electrode section 8 is installed in a distal end portion of the catheter 4 of the high-frequency probe 2 as shown in enlargement in FIG. 2, where the grasping electrode section 8 is used to grasp living tissue (specifically, living tissue of PFO) and apply high-frequency power with the living tissue grasped.

The grasping electrode section 8 which protrudes from a distal end face of the catheter 4 includes needle electrodes 9a shaped like needles and serving as a first electrode and a plate electrode 9b shaped like a plate and serving as a second electrode, where the needle electrodes 9a are two in number, for example, and installed along a longitudinal direction of the catheter 4 facing substantially each other.

Living tissue is grasped by the electrodes as described later. In this case, the living tissue is grasped between the needle electrodes 9a used to puncture the living tissue and the plate electrode 9b facing the needle electrodes 9a. The needle electrodes 9a and plate electrode 9b form a bipolar high-frequency electrode.

The needle electrodes 9a protruding forward from the distal end face of the catheter 4 are passed through lumens 10 provided along the longitudinal direction of the catheter 4.

The two needle electrodes 9a are joined by forming, for example, a U-shape or V-shape a predetermined distance behind the distal end face of the catheter 4. A distal end of a lead wire 11 passing through the catheter 4 is connected to a junction of the two needle electrodes 9a. A rear end of the lead wire 11 is connected to the high-frequency cable 6 in the grasping section 5.

In addition to the lead wire 11, the needle electrodes 9a are connected to an operating member (not shown). Consequently, by advancing or withdrawing a proximal side of the operating member via the grasping section 5, the surgeon can protrude or retract the needle electrodes 9a from/into the lumens 10 in the catheter 4.

On the other hand, the plate electrode 9b is connected with two wires 12 at a proximal end. On the proximal side, the two wires 12 are passed through lumens 13 in the catheter 4.

Again, the two wires 12 are joined by forming, for example, a U-shape or V-shape a predetermined distance behind the distal end face of the catheter 4, as in the case of the two needle electrodes 9a. A distal end of a lead wire 14 passing through the catheter 4 is connected to a junction of the two wires 12. A rear end of the lead wire 14 is connected to the high-frequency cable 6 in the grasping section 5.

The high-frequency cable 6 is connected to an output connector section 15 of the high-frequency surgical power supply system 3 via the connector 7.

The high-frequency surgical power supply system 3 is connected with a foot switch 16, allowing the surgeon to start or end output of high-frequency power. Also, a display section 17 is installed on a front panel of the high-frequency surgical power supply system 3 to display various information.

Figure 3:
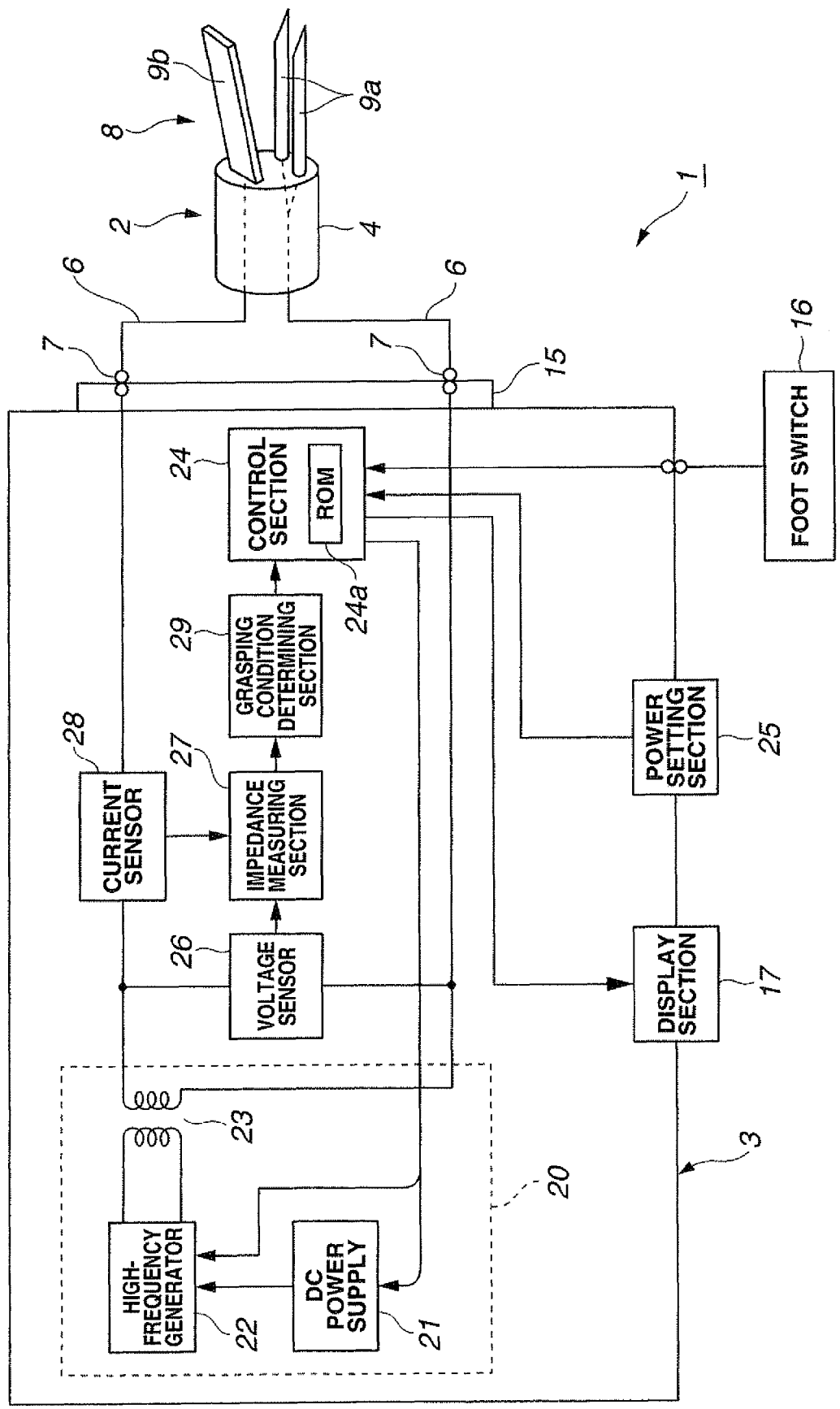

A configuration of the high-frequency surgical power supply system 3 which supplies high-frequency power to the needle electrodes 9a and plate electrode 9b via the connector 7 of the high-frequency probe 2 is shown in FIG. 3.

As shown in FIG. 3, the high-frequency surgical power supply system 3 outputs high-frequency power from a high-frequency power supply section (hereinafter referred to as a power supply section) 20. The power supply section 20 includes a DC power supply circuit 21, a high-frequency generator circuit 22 which generates a high-frequency signal based on DC power supplied from the DC power supply circuit 21, and an output transformer 23 which supplies the high-frequency signal as high-frequency power (output) to a load side from a secondary side insulated from a primary side.

The DC power supply circuit 21 and high-frequency generator circuit 22 are connected to a control section 24 which controls the entire high-frequency surgical PFO closure apparatus 1 including the high-frequency surgical power supply system 3.

The control section 24 is connected with the foot switch 16, the display section 17, and a power setting section 25 which sets a value of high-frequency power.

Information about the value of power set by the power setting section 25 is inputted in the control section 24 and used by the control section 24 to control a value of the DC power supplied to the high-frequency generator circuit 22 and an amplitude and the like of the high-frequency signal generated by the high-frequency generator circuit 22. The control section 24 performs control so as to keep the value of the high-frequency power outputted from the power supply section 20 at a set value of power, i.e., at a set power level.

A CPU (not shown) of the control section 24 controls a process in FIG. 6 (described later) according to a program stored, for example, in a ROM (or flash memory) 24a.

As described later, according to the present embodiment, when the foot switch 16 is turned on, a grasping condition of the grasping electrode section 8 is determined using low power before a procedure is started at the set power level.

In this way, when determining the grasping condition, the control section 24 sets the value of the high-frequency power outputted from the power supply section 20 sufficiently smaller than the value of power used for the actual procedure. Based on a result of the determination, the control section 24 either permits or prohibits output at the set value of power (set power level). That is, the control section 24 controls the high-frequency power supply at the set power level based on the result of the determination.

A voltage sensor 26 is connected between two output terminals of the power supply section 20 to detect voltage of the high-frequency signal between the two output terminals of the power supply section 20. The voltage sensor 26 outputs information about a value of the detected voltage to the impedance measuring section 27.

The two output terminals of the power supply section 20 are connected to respective output terminals of the output connector section 15, with a current sensor 28 being connected in series between one of the two output terminals of the power supply section 20 and the corresponding output terminal.

The current sensor 28 outputs information about a detected current value to the impedance measuring section 27. Based on the inputted voltage value and current value, the impedance measuring section 27 supplies high-frequency power to living tissue of a PFO and measures (or calculates) an impedance value with the living tissue acting as a load. The voltage sensor 26 and current sensor 28 detect the voltage value and current value, for example, in sync with each other. Even when the phases between voltage value and current value are different with each other, the impedance measuring section 27 measures the impedance value on the load side with high accuracy.

The impedance value calculated by the impedance measuring section 27 is inputted in a grasping condition determining section 29.

The grasping condition determining section 29 determines a grasping condition regarding how the grasping electrode section 8 in a distal end portion of the high-frequency probe 2 is grasping the PFO based on the inputted impedance value and outputs a determination result to the control section 24.

In determining the grasping condition, the grasping condition determining section 29 refers to a reference impedance value prestored in its internal memory as a reference threshold.

The reference impedance value (40Ω in a concrete example described later) between the needle electrodes 9a and plate electrode 9b of the grasping electrode section 8 is prestored in the internal memory, having been determined based on an impedance value (first impedance value) measured when practically only the living tissue of the PFO is grasped between the needle electrodes 9a and plate electrode 9b, and an impedance value (second impedance value) measured when there is an amount of blood equal to or larger than a predetermined permissible amount between the needle electrodes 9a and plate electrode 9b.

The impedance value of the living tissue is higher (larger) than the impedance value of the blood. The grasping condition determining section 29 compares the measured impedance value with the reference impedance value, and thereby determines whether the living tissue of the PFO is grasped by the entire grasping electrode section 8 as intended or grasped only by a distal end portion of the grasping electrode section 8 contrary to the intention.

In the former case, the control section 24 determines that the grasping condition is suitable for surgery and makes the power supply section 20 output the set value of high-frequency power (set power level). In the latter case, the control section 24 determines that the grasping condition is unsuitable for surgery and keeps the power supply section 20 from outputting the set value of high-frequency power, i.e., prohibits output of the set value of high-frequency power.

In the present embodiment, to perform a PFO closure procedure to close a PFO in the heart using high-frequency power, a PFO 31 in the heart 30 will be described with reference to FIG. 4.

Figure 4:
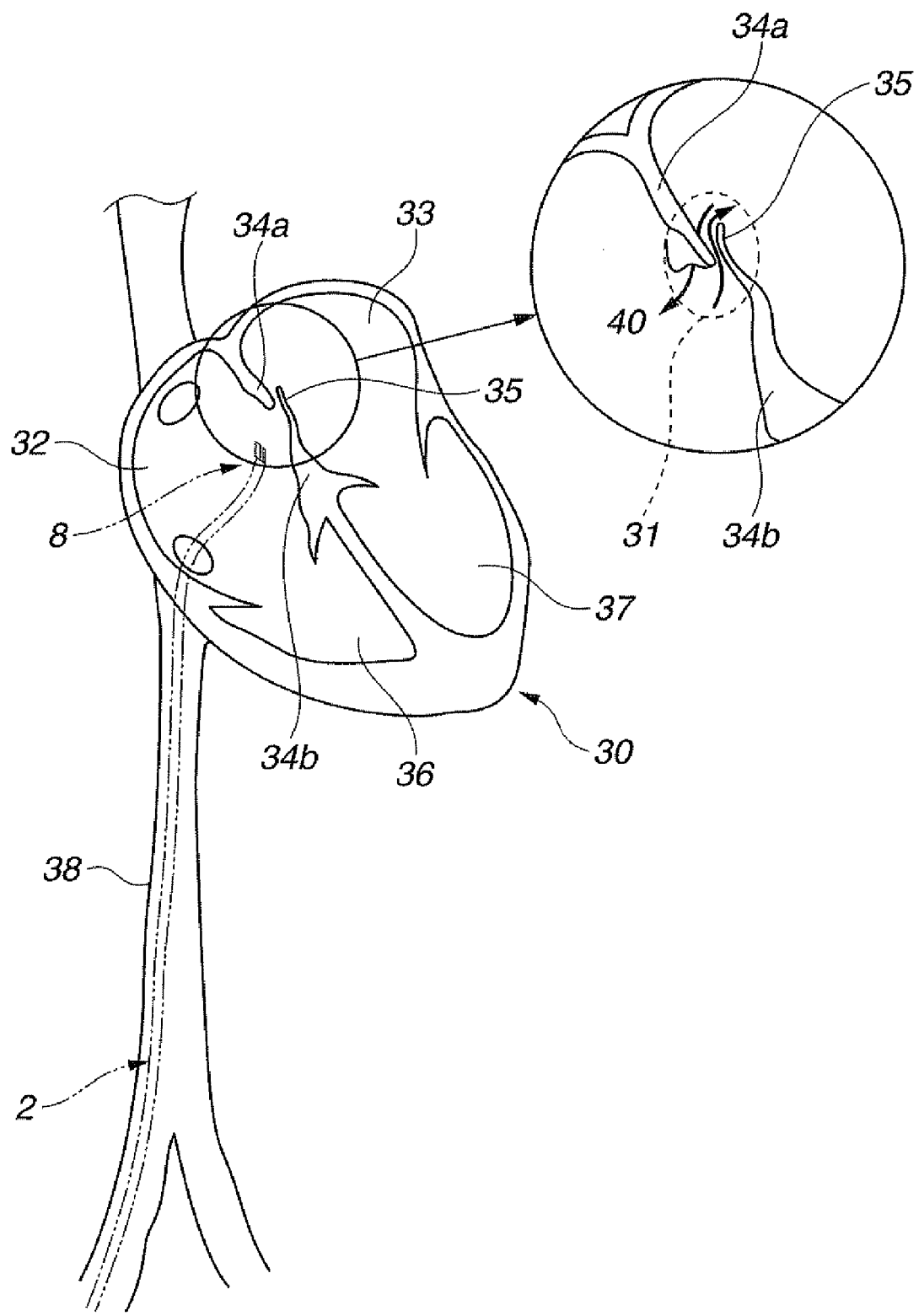

As shown in FIG. 4, the PFO 31 is found in part of the atrial septa 34a and 34b which separate the right atrium 32 from the left atrium 33 in the heart 30. The PFO 31 corresponds to a condition in which valvula foraminis ovalis (also known as the septum primum) 35 remains separated from the atrial septum (septum secondum) 34a. Blood 40 flows around the PFO 31 as indicated by arrows.

Besides, the right ventricle 36 and left ventricle 37 are located under the right atrium 32 and left atrium 33, respectively.

According to the present embodiment, to close the PFO 31 using the high-frequency probe 2 which has flexibility, the high-frequency probe 2 is passed through, for example, the inferior vena cava 38 communicated with the right atrium 32, as indicated by two-dot-chain lines.

Figure 5:
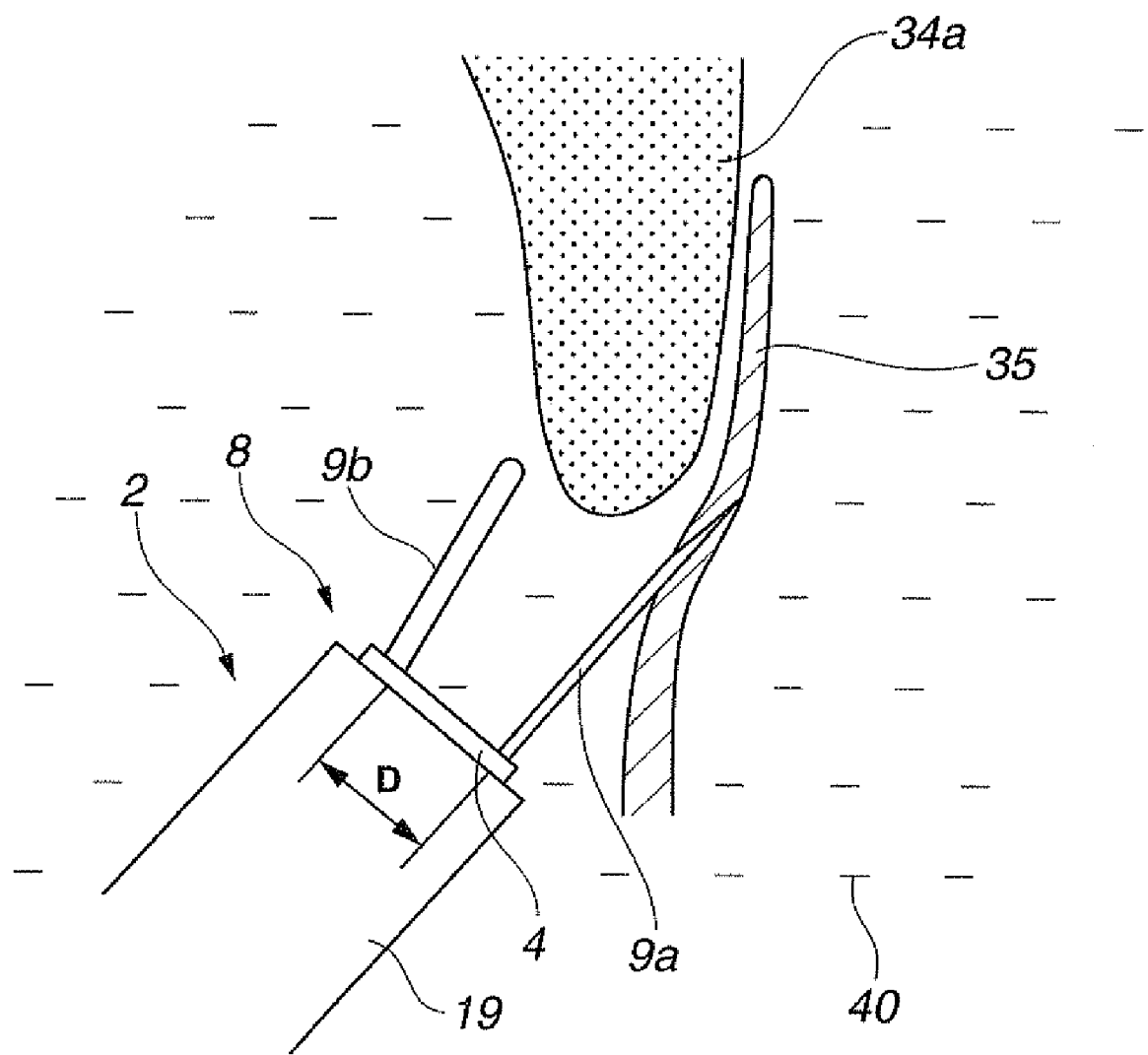

A distal side of the high-frequency probe 2 is inserted in the right atrium 32 through an opening communicated with the right atrium 32, the grasping electrode section 8 on the distal side of the high-frequency probe 2 is protruded toward the PFO 31 as shown in FIG. 5, and the needle electrodes 9a is stuck into the valvula foraminis ovalis 35. Incidentally, reference numeral 40 in FIG. 5 denotes blood.

A distance D from a plane which includes the two parallel needle electrodes 9a to the plate electrode 9b is set to approximately coincide with thickness of an end of the targeted atrial septum 34a as shown in FIG. 5. Thus, by adjusting orientation of the grasping electrode section 8 shown in FIG. 5 and moving the grasping electrode section 8 until the distal end face of the catheter 4 hits an end of the atrial septum 34a, it is possible to grasp the atrial septum 34a by the grasping electrode section 8 with the valvula foraminis ovalis 35 kept in close contact with the atrial septum 34a as shown in FIG. 7A.

Figure 7A:
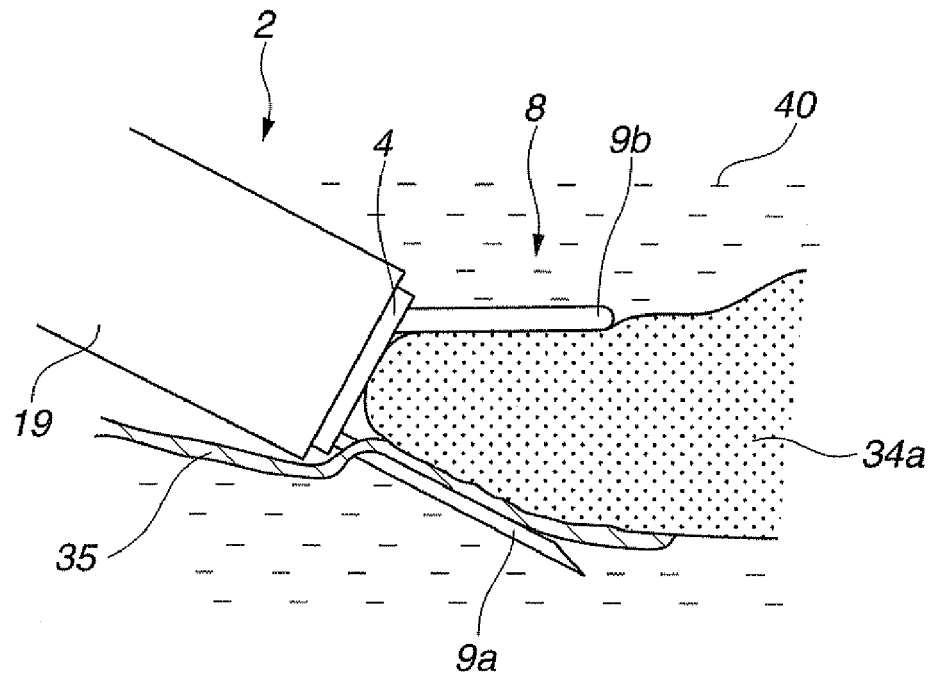
FIG. 7A is an explanatory diagram showing the high-frequency probe which has grasped a PFO ideally.

After the needle electrodes 9a are stuck into the valvula foraminis ovalis 35, by pressing the valvula foraminis ovalis 35 further against the atrial septum 34a, ideally such a grasping condition is established that the end of the atrial septum 34a is grasped by the needle electrodes 9a and plate electrode 9b over the length of the needle electrodes 9a and plate electrode 9b as shown in FIG. 7A.

Then, according to the present embodiment, it is determined whether the grasping condition is suitable for carrying out a closure procedure by supplying (applying) high-frequency power.

Next, a surgical method for closing the PFO 31 using the high-frequency surgical PFO closure apparatus 1 according to the present embodiment will be described with reference to FIG. 6.

First, the surgeon connects the connector 7 of the high-frequency probe 2 to the output connector section 15 of the high-frequency surgical power supply system 3 as shown in FIG. 1. Then, the surgeon makes settings and the like for the power used in procedures, i.e., the set power level.

Figure 6:
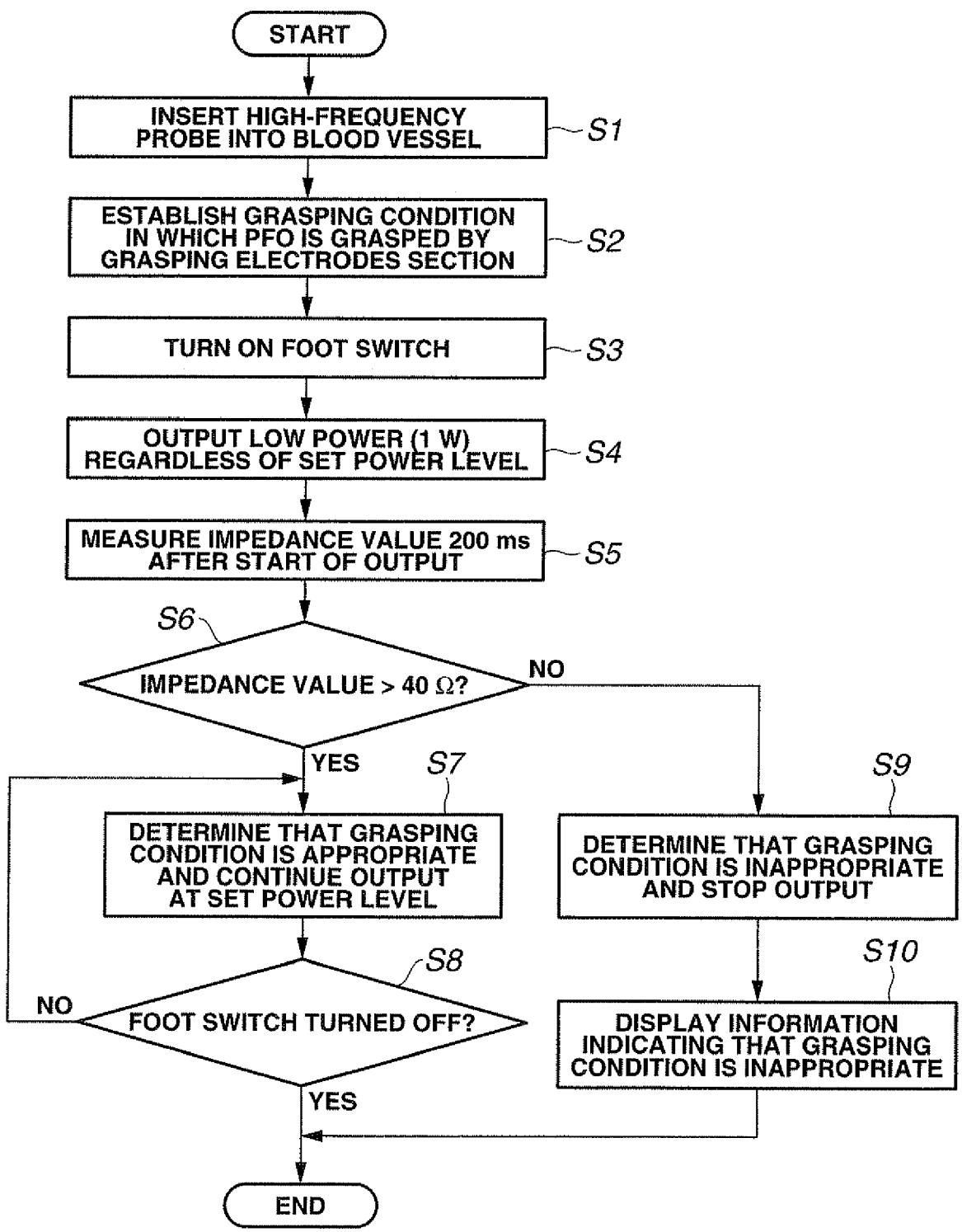

Next, as shown in Step S1 in FIG. 6, the surgeon inserts the high-frequency probe 2 into the blood vessel of the inferior vena cava 38 as shown in FIG. 4. Then, the surgeon inserts a distal end of the high-frequency probe 2 into the heart 30 by monitoring radiographic images or the like via an x-ray CT system.

In this case, since the needle electrodes 9a protrude from a distal end face of the high-frequency probe 2, the surgeon retracts needle electrodes 9a at least to inside the distal end face of the high-frequency probe 2 using the operating member.

A sliding catheter 19 (see FIG. 5) constructed to be slidable may be installed outside the high-frequency probe 2 and the high-frequency probe 2 may be inserted with the needle electrodes 9a and plate electrode 9b housed in the sliding catheter 19.

As shown in Step S2, while monitoring radiographic images or the like via the x-ray CT system, in the heart 30, the surgeon protrudes the needle electrodes 9a of the high-frequency probe 2 forward, sticks distal ends of the needle electrodes 9a into the valvula foraminis ovalis 35 as shown in FIG. 5, and establishes a grasping condition (performs positioning) such that the PFO 31 will be grasped by the needle electrodes 9a and plate electrode 9b as shown in FIG. 7A.

Next, as shown in Step S3, the surgeon turns on the foot switch 16 by depressing it. When the foot switch 16 is turned on, the control section 24 outputs high-frequency power at a low power level (e.g., 1 W) regardless of the set power level, as shown in Step S4.

As shown in Step S5, 200 ms after start of output, the impedance measuring section 27 measures an impedance value based on measurements made by the voltage sensor 26 and current sensor 28. The reason why impedance measurements are taken after a lapse of 200 ms is to reduce the effect of transient response.

The measured impedance value is inputted in the grasping condition determining section 29. As shown in Step S6, the grasping condition determining section 29 determines whether the measured impedance value is larger than the reference impedance (40Ω) and thereby determines whether the grasping condition is appropriate.

If the measured impedance value is larger than 40Ω, as shown in Step S7, the grasping condition determining section 29 determines that the grasping condition in which the high-frequency probe 2 is grasping the PFO 31 is appropriate (or OK). Then, the grasping condition determining section 29 sends the determination result to the control section 24. The control section proceeds with high-frequency power output at the set power level subsequently. In other words, the control section starts high-frequency output at the set power level.

Specifically, high-frequency power is supplied to the grasping electrode section 8 at the set power level under conditions shown in FIG. 7A. Then, the surgeon starts (proceeds with) a procedure for joining the atrial septum 34a and the valvula foraminis ovalis 35 using high-frequency cauterization.

When it is determined in Step S7 that the grasping condition is appropriate, the determination result may be announced to the surgeon by being displayed in the display section 17. Also, information about high-frequency output at the set power level may be displayed or otherwise announced to the surgeon.

In the next Step S8, output is continued at the set power level in Step S7 until the foot switch 16 is turned off.

After a lapse of time required for the procedure, the surgeon turns off the foot switch 16. When the foot switch 16 is turned off, the procedure is finished.

On the other hand, if it is determined in Step S6 that the measured impedance value is 40Ω or below, the grasping condition determining section 29 determines that the grasping condition in which the high-frequency probe 2 is grasping the PFO 31 is inappropriate or not good and stops high-frequency output at the set power level as shown in Step S9. According to the present embodiment, high-frequency output at the low power level is also stopped. Also, as shown in Step S10 the display section 17 (which has a function of an announcement section) displays information indicating that the grasping condition is inappropriate. Thus, operation shown in FIG. 6 is finished.

Incidentally, the announcement in Step S10 and the like is not limited to display in the display section 17, but information about the inappropriate grasping condition may be announced by sound.

Figure 7B:
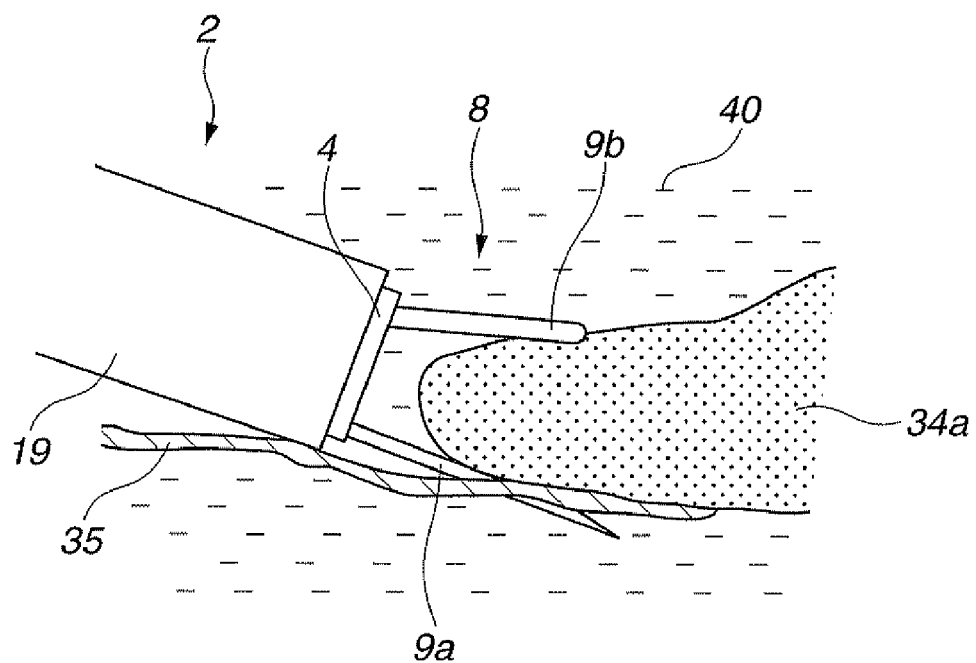
FIG. 7B is an explanatory diagram showing the high-frequency probe which has failed to grasp a PFO ideally.

FIGS. 7A and 7B show ideal grasping and nonideal or inappropriate grasping of the PFO 31 by the high-frequency probe 2, respectively.

In FIG. 7A, the grasping electrode section 8 of the high-frequency probe 2 is grasping the PFO 31 deeply between the electrodes. When the impedance value is measured in this condition, most of high-frequency current flows only through the living tissue, i.e., the PFO 31, resulting in a relatively high measured impedance value (specifically, somewhere around 70Ω).

When application of high-frequency power is continued in this condition, most of high-frequency current flows through the living tissue, heating the PFO 31 and its surroundings and thereby enabling the closure procedure.

In the case of inappropriate grasping shown in FIG. 7B, the high-frequency probe 2 is not grasping the PFO 31 deeply between the electrodes. Consequently, the blood 40 enters the root of the high-frequency probe 2.

If the impedance value is measured in this condition, most of high-frequency current flows through the blood 40, resulting in a relatively low measured impedance value (specifically, somewhere around 20Ω). Also, when application of high-frequency power is continued in this condition, most of high-frequency current flows through the blood 40, failing to sufficiently heat the PFO 31 and its surroundings and thereby preventing the closure procedure from going smoothly.

The high-frequency surgical power supply system 3 according to the present embodiment determines differences in grasping condition based on magnitude of the measured impedance value.

As described with reference to the flowchart in FIG. 6, when the grasping condition is as shown in FIG. 7A, application of high-frequency power is started (continued) at the set power level to carry out the procedure for closing the PFO 31. On the other hand, when the grasping condition is as shown in FIG. 7B, the application of high-frequency power is stopped. When the application of high-frequency power is stopped, information about the inappropriate grasping condition is displayed as shown in Step S10, prompting the surgeon to check how the PFO 31 is punctured. According to the present embodiment, when the surgeon tries to grasp the PFO 31, the grasping condition regarding how the PFO 31 is grasped by the high-frequency probe 2 is determined by measuring the impedance at that time. This prevents the surgeon from carrying out the procedure under inappropriate grasping condition and allows the surgeon to carry out the procedure for closing the PFO 31 smoothly under an appropriate grasping condition.

Next, a variation of the present embodiment will be described.

Figure 8:
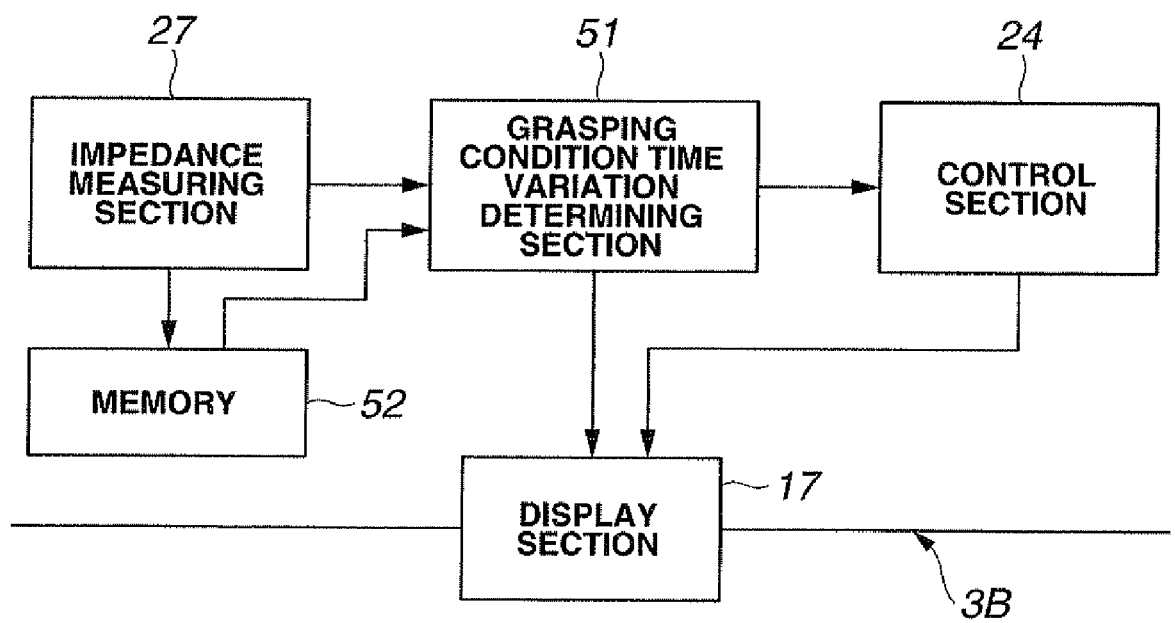

According to the present variation, when a grasping condition in which the grasping electrode section 8 grasps the PFO 31 is established, the impedance is measured and time variation of the measured impedance is monitored. For that, a partial configuration of a high-frequency surgical power supply system 3B according to the present variation is shown in FIG. 8. The high-frequency surgical power supply system 3B shown in FIG. 8 has a grasping condition time variation determining section 51 instead of the grasping condition determining section 29 of the high-frequency surgical power supply system 3 shown in FIG. 3.

The impedance value measured by the impedance measuring section 27 is inputted to the grasping condition time variation determining section 51 and stored temporarily in a memory 52. The grasping condition time variation determining section 51 determines the grasping condition in the manner described above from the impedance value measured by the impedance measuring section 27, compares the measured impedance value with the impedance value stored in the memory 52, and thereby determines time variation of the grasping condition based on changes in the impedance value.

Also, the grasping condition time variation determining section 51 displays the time variation of measured impedance values in the display section 17 (which may be via the control section 24). The grasping condition time variation determining section 51 also displays a reference impedance value in the display section 17 in order for the surgeon to see the grasping condition at the time based on impedance information.

The rest of the configuration is the same as the first embodiment.

Figure 9:
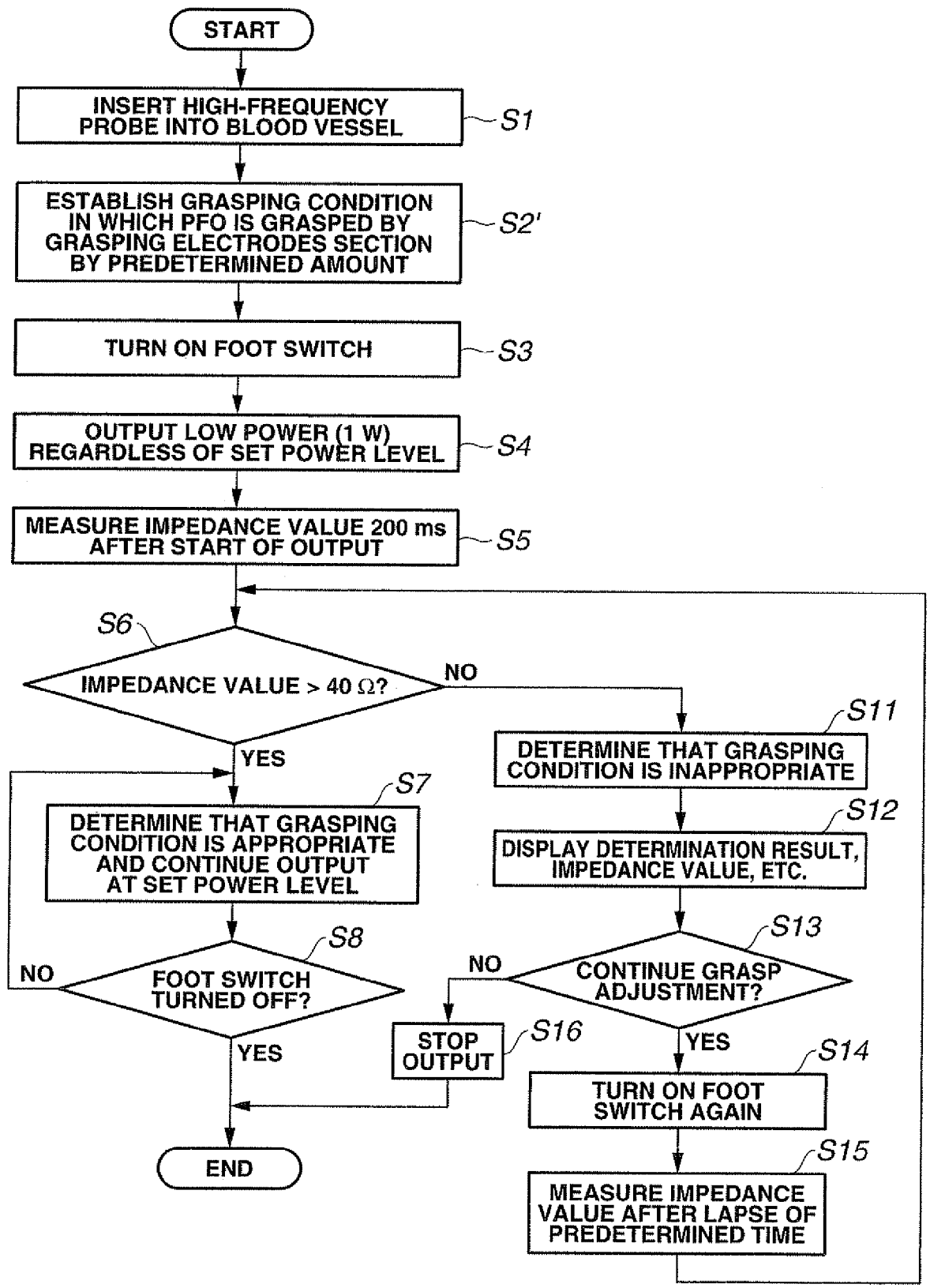

FIG. 9 is a flowchart of operation according to the present variation. The flowchart in FIG. 9 is the same as the flowchart in FIG. 6 in terms of Steps S1 to S8.

In FIG. 9, however, in Step S2' next to Step S1, the surgeon establishes a grasping condition in which the PFO 31 is grasped by the grasping electrode section 8 by a predetermined amount before turning on the foot switch 16 in Step S3.

It is assumed here that the grasping condition in which the PFO 31 is grasped by the predetermined amount occurs before the surgeon completes the process of grasping (alternatively, this condition may occur when the process of grasping is completed as shown in FIG. 7A). That is, measurement of the impedance value is started when the surgeon is in the process of establishing appropriate grasping condition of the grasping electrode section 8 and the surgeon makes subsequent grasping-condition adjustments with reference to the measured impedance value.

In Steps S4 to S6, the impedance value is determined in the same manner as in FIG. 6.

If it is determined in Step S6 that the measured impedance value exceeds 40Ω, Steps S7 and S8 are carried out as in the case of FIG. 6.

If it is determined in Step S6 that the measured impedance value is 40Ω or below, the grasping condition time variation determining section 51 determines in Step S11 that the grasping condition is inappropriate.

Also, as shown in Step S12, the grasping condition time variation determining section 51 displays a determination result, i.e., information that the grasping condition is inappropriate, as well as the impedance value and the like in the display section 17.

Next, as shown in Step S13, the grasping condition time variation determining section 51 asks the surgeon to select whether to continue grasp adjustments of the grasping electrode section 8. To select continuation, the surgeon turns on the foot switch 16 again as shown in Step S14. The ON signal is transmitted from the control section 24 to the impedance measuring section 27 and the grasping condition time variation determining section 51.

Next, as shown in Step S15, the impedance measuring section 27 measures impedance a predetermined time after the surgeon selected continuation. The measured impedance value is inputted in the grasping condition time variation determining section 51 and temporarily stored in the memory 52.

After Step S15, the flow returns to the determination process in Step S6 where the grasping condition time variation determining section 51 determines whether the measured impedance value is larger than 40Ω.

Incidentally, the value of the predetermined time may be made adjustable to allow for the time required by the surgeon to make grasping-condition adjustments and thereby more appropriately establish the grasping condition in which the PFO 31 is grasped by the grasping electrode section 8.

In this case, the measured impedance value is displayed in the display section 17 after each lapse of the predetermined time, i.e., on a predetermined cycle. Thus, when the surgeon makes grasping-condition adjustments and thereby changes the grasping condition, the impedance value displayed in the display section 17 changes accordingly. Incidentally, time variation of the impedance value may also be displayed in the display section 17 as described later.

The surgeon further makes grasp adjustments. By looking at change of the impedance value displayed consequently in the display section 17 and a tendency of the change in the impedance value, the surgeon can see whether the surgeon is on the right track in achieving an appropriate grasping condition.

On the other hand, if the surgeon does not select continuation in Step S13, the control section 24 stops the high-frequency output as shown in Step S16 and thereby finishes the process shown in FIG. 9. To indicate that the surgeon does not select continuation, the surgeon may turn off the foot switch 16.

Figure 10:
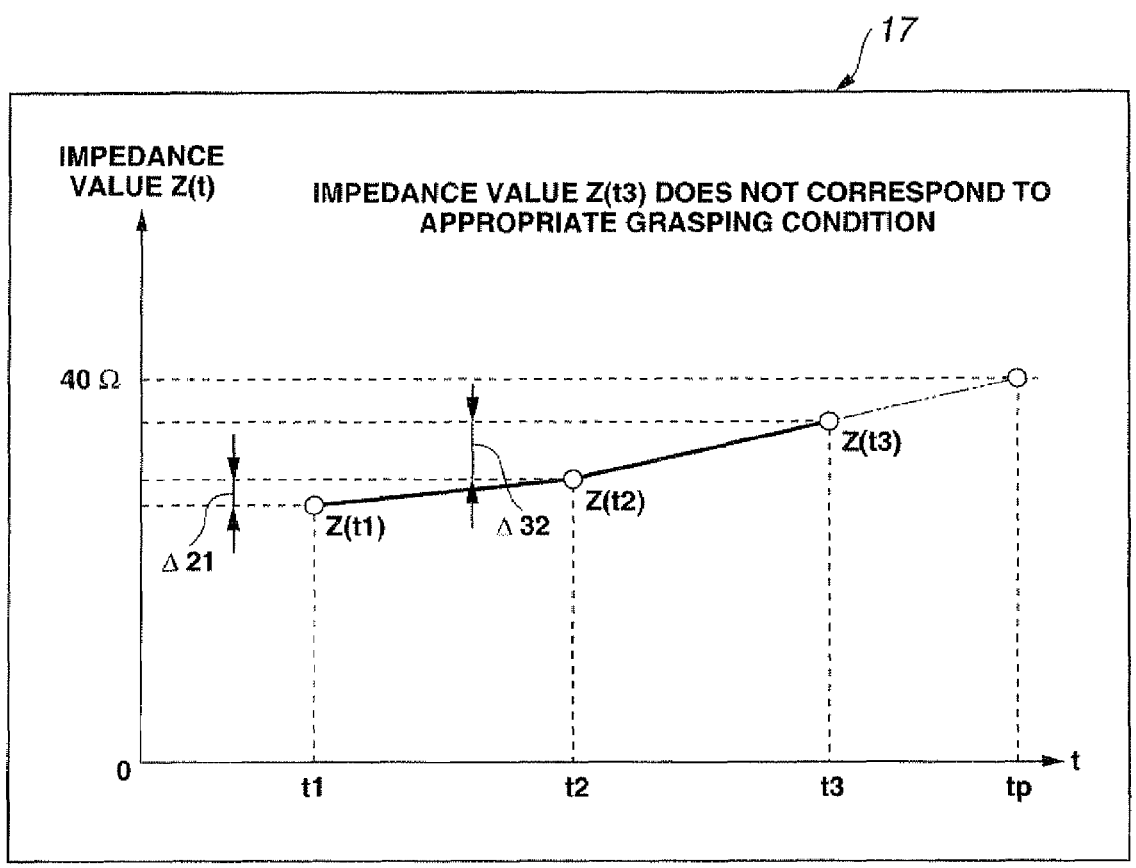

FIG. 10 shows a display example presented in the display section 17 when the surgeon selects continuation in Step S13. In FIG. 10, $Z(t1)$ represents the impedance value measured first in Step S6 at time $t1$ and $Z(t2)$ represents the impedance value measured next at time $t2$ when the surgeon selects to continue grasp adjustments in Step S13.

If the surgeon moves the grasping electrode section 8 between times $t1$ and $t2$ or until a later time $t3$ so as to grasp the PFO 31 deeply, the impedance value $Z(t2)$ or $Z(t3)$ may become larger than the earlier impedance value $Z(t1)$.

Incidentally, the display example in FIG. 10 shows a state up to time $t3$. It is shown that the impedance value at time $t3$ does not correspond to an appropriate grasping condition.

During grasp readjustments, since the corresponding impedance value is displayed, by looking at the contents of display, the surgeon can easily see whether the surgeon is in the process of achieving an appropriate grasping condition. Consequently, the surgeon can carry out the procedure smoothly.

In FIG. 10, when the grasp is readjusted, information about the time variation of the impedance value is displayed in more detail by displaying amounts of time variation in the impedance value $Z(t)$ such as $\Delta 21=(Z(t2)-Z(t1))$ and $\Delta 32$.

Alternatively, a rate of time variation in the impedance value $Z(t)$ such as $\Delta'21=\Delta 21/Z(t1)$ or $\Delta'21=\Delta 21/Z(t2)$ may be displayed.

Also, the grasping condition time variation determining section 51 may estimate the time when the impedance value (40Ω in the concrete example) determined to correspond to an appropriate grasping condition will be obtained, based on the rate of time variation in the impedance value $Z(t)$, and display information about the time in the display section 17.

In FIG. 10, an estimated time at which an appropriate grasping condition will be achieved is represented by $tp$, where the estimated time is found by extending a time variation line (two-dot-chain line) which connects the impedance values $Z(t2)$ and $Z(t3)$ at times $t2$ and $t3$. Incidentally, the estimated time is found by the grasping condition time variation determining section 51, but may be found by the control section 24.

After the surgeon adjusts the grasping condition, the corresponding estimated time $tp$ is displayed, making it easier for the surgeon to establish an appropriate grasping condition of the grasping electrode section 8.

A configuration according to a second embodiment described below and different from the one described above may be used to carry out a PFO closure procedure using high-frequency power while preventing development of blood clots.

Second Embodiment

Figure 11:
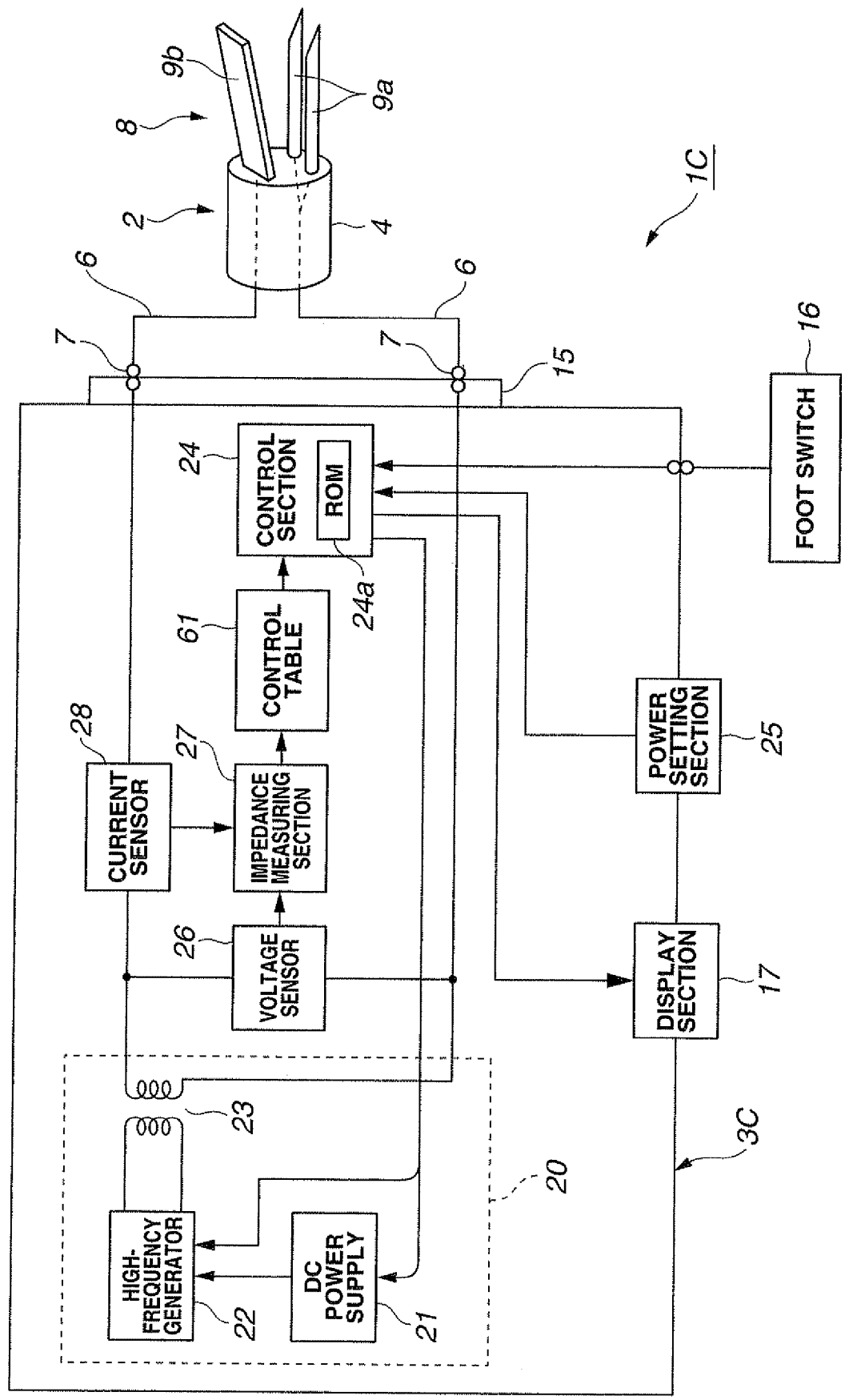
FIG. 11 is a block diagram showing a configuration of a high-frequency surgical PFO closure apparatus according to a second embodiment of the present invention.

FIG. 11 shows a configuration of a high-frequency surgical PFO closure apparatus 1C according to a second embodiment of the present invention. The high-frequency surgical PFO closure apparatus 1C differs from the high-frequency surgical PFO closure apparatus 1 in that the high-frequency surgical PFO closure apparatus 1C includes a high-frequency surgical power supply system 3C which has a control table 61 instead of the grasping condition determining section 29 of the high-frequency surgical power supply system 3 shown in FIG. 3.

The control table 61 prestores duty cycle information for use in supplying a set level of high-frequency power by turning on and off the high-frequency power based on a measured impedance value.

The control section 24 reads a duty cycle corresponding to the measured impedance value from the control table 61 and uses high-frequency power at the given duty cycle for the procedure. Incidentally, the control table 61 stores information to the effect that output will be stopped when the impedance value reaches or exceeds a predetermined value (specifically, 200Ω).

Next, operation of the present embodiment will be described with reference to a flowchart in FIG. 12. Steps S21 to S25 are the same as Steps S1 to S5 in FIG. 6. After impedance is measured in Step S25, the control section 24 determines the duty cycle (ON/OFF times) corresponding to the measured impedance value from the control table 61 in Step S26.

Figure 14:
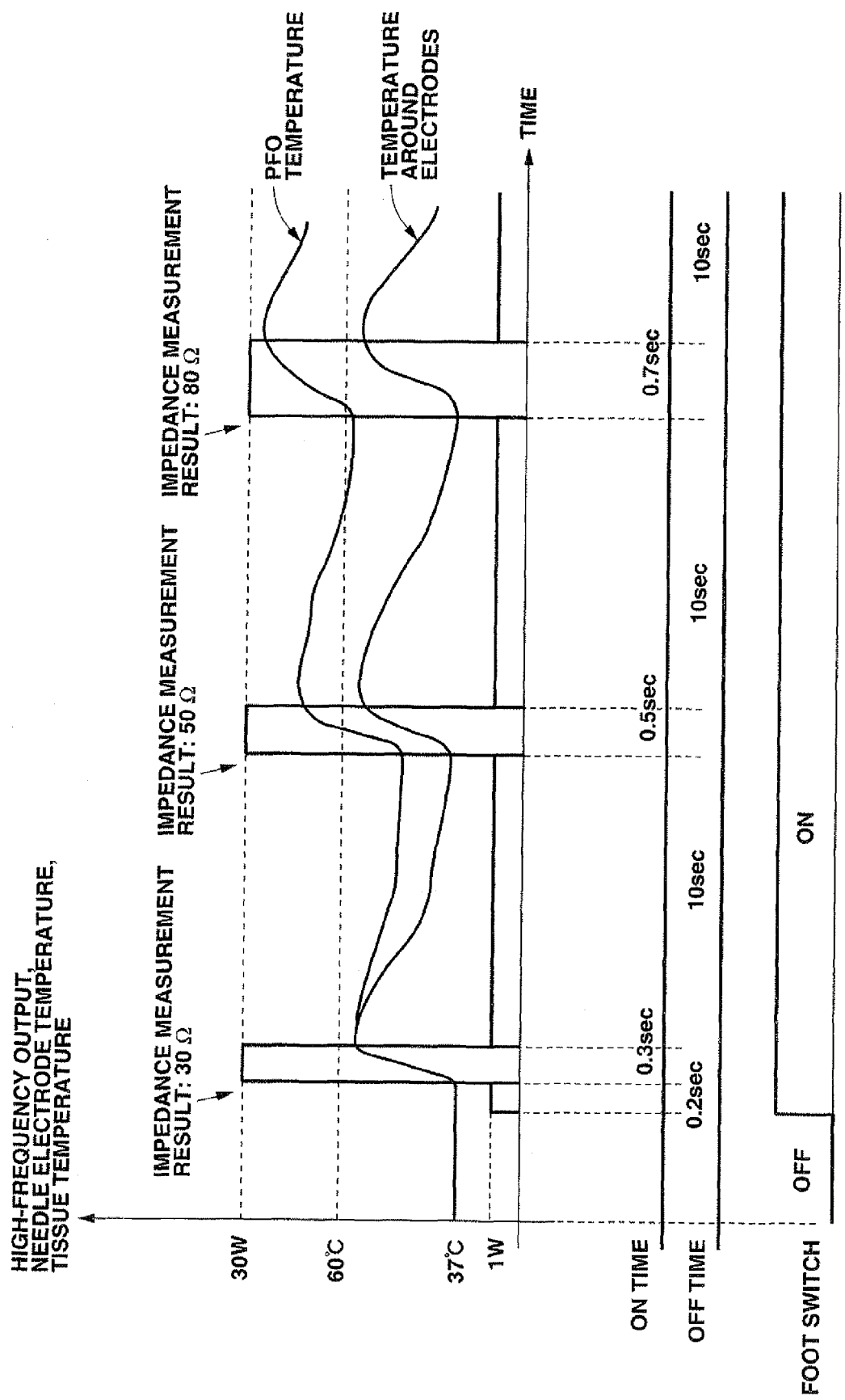
FIG. 14 is an operation chart according to the second embodiment.

FIG. 14 described later is an operation chart in which the set power level is 30 W and the impedance value measured first is 30Ω. In this case, according to the control table 61, the ON time at the set power level is 0.3 sec. and the OFF time is 10 sec.

Next, in Step S27, the control section 24 outputs high-frequency waves at the set power level for the period of ON time (0.3 sec. in this case) of the determined duty cycle. As shown in Step S28, the control section 24 determines whether the measured impedance value reaches 200Ω during output lasting for the period of ON time.

If the measured impedance value is less than 200Ω, the control section 24 produces output at 1 W for the period of the OFF time determined based on the control table 61, as shown in Step S29. Then, as shown in Step S30, the impedance measuring section 27 measures the impedance value again and the flow returns to Step S26.

In this way, unless the measured impedance value reach 200Ω, a high-frequency cauterization procedure is performed at the set power level for the period of ON time corresponding to the measured impedance. When the measured impedance value reaches 200Ω, the flow goes to Step S31. In Step S31, the control section 24 determines that the cauterization is complete, stops output and announces the completion of cauterization to the surgeon. Then, the procedure shown in FIG. 12 is finished.

FIG. 13 shows an example of information contained in the control table 61. As shown in FIG. 13, the control table 61 stores information about ON/OFF times classified by set output and measured impedance value.

Figure 12:
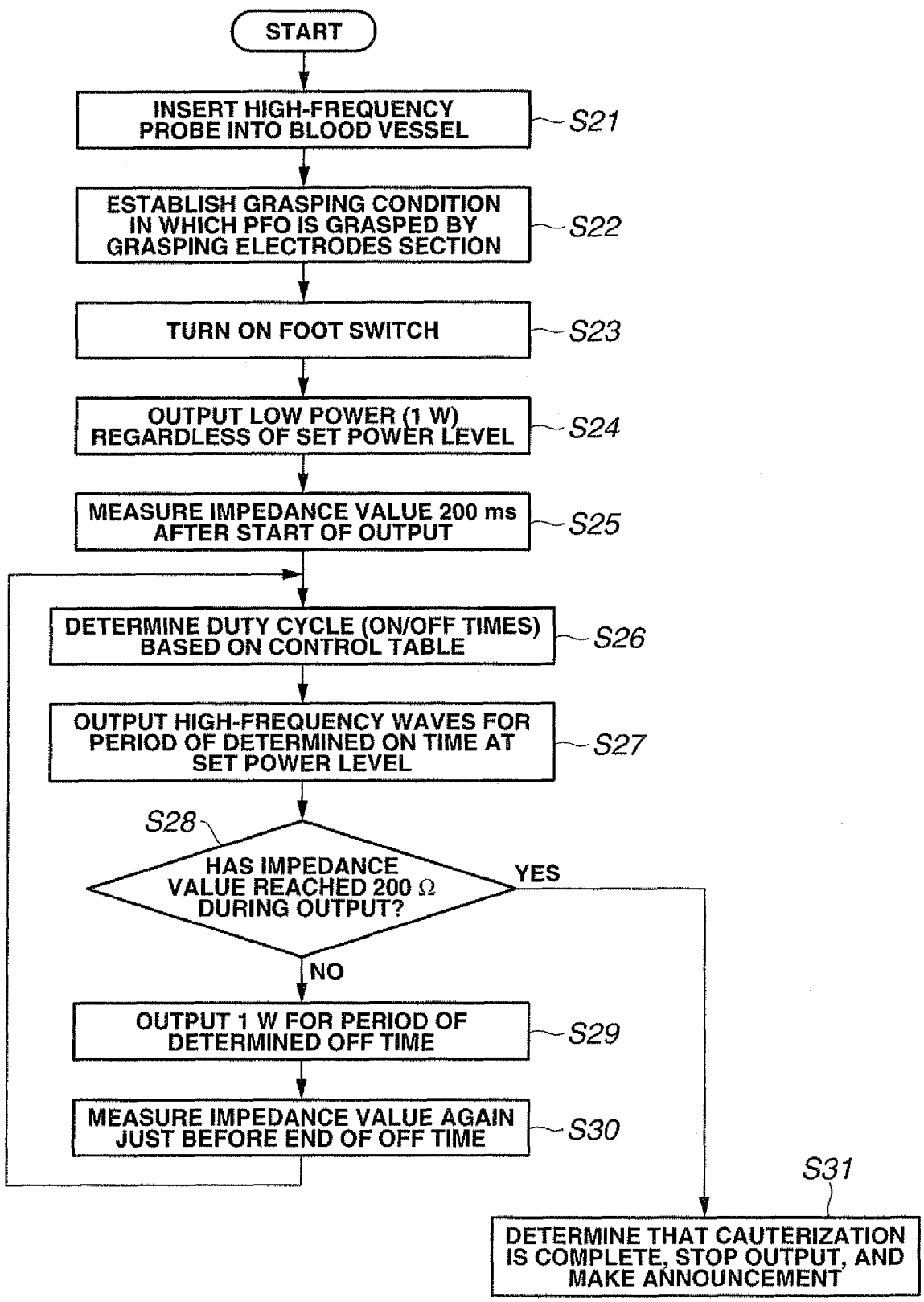
FIG. 12 is a flowchart showing processing procedures of a high-frequency surgical method according to the second embodiment.

FIG. 14 is an operation chart which results when a procedure is carried out according to the flowchart in FIG. 12. In the operation chart, the abscissa represents time while the ordinate represents high-frequency output (power), needle electrode temperature (temperature around the electrodes), and tissue temperature (PFO temperature). The set power level is 30 W.

When the foot switch 16 is turned on, the impedance is measured at a power of 1 W. In the example of FIG. 13, the measured impedance value is 30Ω. In this case, according to the control table 61 in FIG. 14, the ON time is 0.3 sec. and the OFF time is 10 sec. at the set power level.

Then, high-frequency waves are outputted at the set power level (i.e., 30 W) for 0.3 sec. In FIG. 14, both needle electrodes and PFO are heated and their temperatures rise from their original temperatures of 37° C. Subsequently, during the OFF period of 10 sec., the temperatures fall. For the following reasons, the needle electrodes become colder than the PFO.

It is assumed that an impedance measurement taken just before the end of the 10-second OFF period indicates that the impedance value is 50Ω.

In this case, according to the control table 61 in FIG. 13, the ON time at the set power level is 0.5 sec. and the OFF time is 10 sec.

Then, high-frequency waves are outputted at the set power level (i.e., 30 W) for 0.5 sec. It is assumed that an impedance measurement taken just before the end of the 10-second OFF period indicates that the impedance value is 80Ω.

In this case, according to the control table 61 in FIG. 13, the ON time at the set power level is 0.7 sec. and the OFF time is 10 sec. The temperature of the needle electrodes is kept below a temperature at which blood clots may develop.

FIG. 14 shows a temperature control example in which the needle electrodes are kept below 60° C.

In this way, when the measured impedance reaches 200Ω, the high-frequency cauterization procedure is terminated.

An advantage of applying high-frequency output intermittently in the above manner during a procedure will be described. As described above, during a high-frequency cauterization procedure for closing the PFO 31 carried out in the blood 40 in the heart 30, blood clot development is caused mainly depending on the duration of high-frequency cauterization and temperature of the blood 40 raised by the high-frequency cauterization. Thus, even if the temperature rises, by reducing the duration of the temperature rise, the temperature of the blood 40 around contact surfaces between the blood 40 and electrodes is kept below a predetermined temperature at which blood clots will start to develop.

Generally, to close the PFO 31, it is necessary to heat the PFO 31 to or above 60° C. Also, it is known that blood clots develop at and above approximately 60° C.

Thus, if high-frequency waves are outputted by setting the ON/OFF times in such a way as to maintain the temperature around the electrodes to or below 60° C., and the temperature at the junction of the PFO 31 to or above 60° C. as with the present embodiment, it is possible to join (close) the PFO 31 without causing blood clots.

Incidentally, although the ON/OFF times are set anew for each output in the above description, for example, the ON/OFF times may be fixed regardless of the impedance value. Also, certain effects can be achieved if an impedance measurement is taken only once at the beginning and the same ON/OFF times are used subsequently.

By outputting high-frequency power intermittently, the present embodiment makes it possible to carry out a procedure for closing the PFO 31 while preventing temperature rises around the electrodes and development of blood clots.

The numerical values cited herein are only exemplary and are not meant to restrict the present invention.

In the embodiment described above, the high-frequency probe 2 may include positioning/holding means 60 which has a positioning part 61 and a holding part 62 such as described in FIG. 25 of PCT International Publication No. WO 2007/100067.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A high-frequency surgical apparatus for closure of patent foramen ovale, the high-frequency surgical apparatus being used to treat patent foramen ovale in the heart, comprising:
    first and second electrodes which grasp living tissue of the patent foramen ovale, at least one of the first and second electrodes being capable of puncturing the living tissue;
    a high-frequency power supply section which supplies high-frequency power to the living tissue via the first and second electrodes;
    an impedance measuring section which measures an impedance value with the living tissue acting as a load when high-frequency power is supplied to the living tissue from the high-frequency power supply section at a second high-frequency power level which is smaller than a first high-frequency power level needed to treat the patent foramen ovale;
    a grasping condition determining section which determines a grasping condition regarding how the living tissue is grasped in blood by the first and second electrodes by setting as a threshold an impedance value obtained when an amount of blood equal to or larger than a predetermined amount exists between the first and second electrodes and comparing the impedance value measured by the impedance measuring section with the threshold; and
    a control section which, when the grasping condition determining section determines the grasping condition as a grasping condition in which the impedance value measured by the impedance measuring section is equal to or smaller than the threshold, prohibits supply of the high-frequency power to the living tissue at the first high-frequency power level needed to treat the patent foramen ovale, and when the grasping condition determining section determines the grasping condition as a grasping condition in which the impedance value measured by the impedance measuring section is larger than the threshold, starts or permits the supply of the high-frequency power to the living tissue at the first high-frequency power level needed to treat the parent foramen ovale.

2. The high-frequency surgical apparatus for closure of patent foramen ovale according to claim 1, wherein spacing between the first and second electrodes is set to approximately coincide with thickness of the living tissue grasped by the first and second electrodes.

3. The high-frequency surgical apparatus for closure of patent foramen ovale according to claim 1, wherein the living tissue is the septum primum and the septum secondum and the patent foramen ovale is closed using a procedure for joining the septum primum and the septum secondum under the supply of the high-frequency power at a predetermined power level needed to treat the patent foramen ovale.

4. The high-frequency surgical apparatus for closure of patent foramen ovale according to claim 1, wherein at least one of the first and second electrodes is at least one needle electrode shaped like a needle capable of puncturing the living tissue.

5. The high-frequency surgical apparatus for closure of patent foramen ovale according to claim 1, wherein the first and second electrodes are mounted at a distal end of a catheter which has such an outside diameter as to allow the catheter to be inserted into a blood vessel.

6. The high-frequency surgical apparatus for closure of patent foramen ovale according to claim 1, wherein when determining the grasping condition as a grasping condition in which the impedance value measured by the impedance measuring section is equal to or smaller than the threshold, the grasping condition determining section further continues determining the grasping condition of the living tissue on a predetermined cycle.

7. The high-frequency surgical apparatus for closure of patent foramen ovale according to claim 1, further comprising an announcement section which announces information about at least one of the case where the grasping condition determining section determines the grasping condition as a grasping condition in which the impedance value measured by the impedance measuring section is equal to or smaller than a threshold and the case where the grasping condition determining section determines the grasping condition as a grasping condition in which the impedance value measured by the impedance value measuring section is larger than the threshold.

8. The high-frequency surgical apparatus for closure of patent foramen ovale according to claim 1, wherein when determining the grasping condition as a grasping condition in which the impedance value measured by the impedance measuring section is equal to or smaller than the threshold, the grasping condition determining section further continues determining the grasping condition of the living tissue on a predetermined cycle and a display section displays the measured impedance value.

9. The high-frequency surgical apparatus for closure of patent foramen ovale according to claim 1, wherein when determining the grasping condition as a grasping condition in which the impedance value measured by the impedance measuring section is equal to or smaller than the threshold, the grasping condition determining section further continues determining the grasping condition of the living tissue on a predetermined cycle and a display section displays information about time variation of the measured impedance value.

10. The high-frequency surgical apparatus for closure of patent foramen ovale according to claim 1, wherein when determining the grasping condition as a grasping condition in which the impedance value measured by the impedance measuring section is equal to or smaller than the threshold, the grasping condition determining section estimates a time when the determination result of a grasping condition in which the measured impedance value is larger than the threshold is obtained, based on information about time variation of the impedance value measured by the impedance measuring section.

11. A high-frequency surgical apparatus for closure of patent foramen ovale, the high-frequency surgical apparatus being used to treat patent foramen ovale in the heart, comprising:
    first and second electrodes which grasp living tissue of the patent foramen ovale, at least one of the first and second electrodes being capable of puncturing the living tissue;
    high-frequency power supply means which supplies high-frequency power to the living tissue via the first and second electrodes;

impedance measuring means which measures an impedance value with the living tissue acting as a load when high-frequency power is supplied to the living tissue from the high-frequency power supply means at a second high-frequency power level which is smaller than a first high-frequency power level needed to treat the patent foramen ovale;

grasping condition determining means which determines a grasping condition regarding how the living tissue is grasped in blood by the first and second electrodes by setting as a threshold an impedance value obtained when an amount of blood equal to or larger than a predetermined amount exists between the first and second electrodes and comparing the impedance value measured by the impedance measuring means with the threshold; and control means which, when the grasping condition determining section determines the grasping condition as a grasping condition in which impedance value measured by the impedance measuring section is equal to or smaller than the threshold, prohibits supply of the high-frequency power to the living tissue at the first high-frequency power level needed to treat the parent foramen ovale, and when the grasping condition determining section determines the grasping condition as a grasping condition in which the impedance value measured by the impedance measuring section is larger than the threshold, starts or permits the supply of the high-frequency power to the living tissue at the first high-frequency power level needed to treat the patent foramen ovale.

12. The high-frequency surgical apparatus for closure of patent foramen ovale according to claim 1, wherein the first high-frequency power level is set to several tens of watts.

13. The high-frequency surgical apparatus for closure of patent foramen ovale according to claim 1, wherein the second high-frequency power level is set under several watts.

14. The high-frequency surgical apparatus for closure of patent foramen ovale according to claim 1, wherein the first high-frequency power level is set to be ten times greater than the second high-frequency power level or more.

15. The high-frequency surgical apparatus for closure of patent foramen ovale according to claim 1, wherein the threshold is set to 40Ω.

* * * * *